United States Patent
Esham et al.

(10) Patent No.: US 8,046,045 B2
(45) Date of Patent: Oct. 25, 2011

(54) ANATOMICAL FEATURE CONDITION ASSESSMENT SYSTEM USING TISSUE DISPLACEMENT CHARACTERISTICS

(75) Inventors: Matthew Paul Esham, Pennsville, NJ (US); Joan Carol Main, Mountain View, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 941 days.

(21) Appl. No.: 11/745,110

(22) Filed: May 7, 2007

(65) Prior Publication Data

US 2008/0009729 A1 Jan. 10, 2008

Related U.S. Application Data

(60) Provisional application No. 60/746,664, filed on May 8, 2006.

(51) Int. Cl.
*A61B 5/05* (2006.01)
(52) U.S. Cl. .......................... 600/407; 382/128; 128/898
(58) Field of Classification Search .................. 600/411, 600/425, 427, 437, 438, 450, 481; 382/128, 382/131, 173
See application file for complete search history.

(56) References Cited

U.S. PATENT DOCUMENTS

| | | | |
|---|---|---|---|
| 5,568,811 | A | 10/1996 | Olstad |
| 5,669,387 | A | 9/1997 | Mine |
| 5,860,927 | A | 1/1999 | Sakaguchi et al. |
| 5,903,664 | A | 5/1999 | Hartley et al. |
| 6,053,869 | A | 4/2000 | Kawagishi et al. |
| 6,447,453 | B1 | 9/2002 | Roundhill et al. |
| 6,674,879 | B1 | 1/2004 | Weisman et al. |
| 6,961,454 | B2 | 11/2005 | Jolly |
| 7,043,062 | B2 | 5/2006 | Gerard et al. |
| 7,043,063 | B1 | 5/2006 | Noble et al. |
| 2001/0024516 | A1* | 9/2001 | Yoshioka et al. ............. 382/128 |

OTHER PUBLICATIONS

Tedrow U. Wall Motion Abnormality Scores as a Possible Predictor of Response to CRT: Analysis of Echocardiographic Data from the MIRACLE Trial. Medscape Cardiology. Jun. 3, 2004.*
Murta Jr., L. O. et al., "Automatic grading of left ventricular segmental wall motion by an articifical enural network using color kinesis images," *Brazilian Journal of Medical and Biological Research* ISSN: 0100-879X, Jan. 2006, vol. 39(1) 1-7.

(Continued)

*Primary Examiner* — Parikha Mehta
(74) *Attorney, Agent, or Firm* — Alexander J Burke

(57) ABSTRACT

An anatomical feature condition assessment system includes an acquisition processor for acquiring data representing the velocity and direction measurements of individual segments of an anatomical feature of a patient. A repository contains mapping data associating averaged velocity and direction measurements within a predetermined particular segment of the anatomical feature with a set of values. A data processor averages the acquired velocity and direction measurements within the predetermined particular segment of the anatomical feature and uses the mapping data to identify a set of values associated with the averaged acquired velocity and direction measurements. The data processor uses the identified set of values to derive an assessment of the condition of the anatomical feature of the patient.

10 Claims, 10 Drawing Sheets

OTHER PUBLICATIONS

Feigenbaum, MD et al., "Feigenbaum's Echocardiography,"2005, pp. 149-152, Lippincott Williams & Wilkins, Philadelphia, PA USA.

Donatiella, MD et al., "Echocardiographic Equations,"downloaded Apr. 30, 2007 URL: http://www2.umdnj.edu/~shindler/eq2.html#wallm, Wall Motion Score bookmark.

Siemens Medical Solutions, USA, "Cardiac Assessment Microsite,"downloaded Apr. 30, 2007 URL: http://www.smed.com/vvimicrosite/vvi_clinical.htm.Link marked: 'Clear representation of left ventricular rotation with VVI technology.

Fung, Glenn et al., "Sparse Classifiers for Automated Heart Wall Motion Abnormality Detection."

John Jackson, Ph.D., Helene Houle, B.A., R.D.C.S. Ultasound Division, "Syngo Velocity Vector Imaging", whitepaper, Siemens Medical Solutions USA, Inc., May 2006.

* cited by examiner

4 CHAMBER VIEW

2 CHAMBER VIEW

| PLAX - 4 SEGMENT CONFIGURATION | | | | |
|---|---|---|---|---|
| SEGMENT | DEFAULT SEGMENT NAME (CONFIGURABLE) | WALL MOTION SCORE (CONFIGURABLE) | DEFAULT AMPLITUDE M/S (CONFIGURABLE) | DEFAULT DIRECTION (DEGREES) (CONFIGURABLE) |
| 1 | BASAL SEPTUM | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 2 | MID SEPTUM | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 3 | MID POSTERIOR WALL | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 4 | BASAL POSTERIOR WALL | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |

FIG. 8

| PLAX - 6 SEGMENT CONFIGURATION | | | | |
|---|---|---|---|---|
| SEGMENT | DEFAULT SEGMENT NAME (CONFIGURABLE) | WALL MOTION SCORE (CONFIGURABLE) | DEFAULT AMPLITUDE M/S (CONFIGURABLE) | DEFAULT DIRECTION (DEGREES) (CONFIGURABLE) |
| 1 | BASAL SEPTUM | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 2 | MID SEPTUM | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 3 | APICAL SEPTUM | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 4 | APICAL POSTERIOR WALL | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 5 | MID POSTERIOR WALL | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |
| 6 | BASAL POSTERIOR WALL | NORMAL | 3.5 TO 6.0 | 0 TO 90; 270 TO 360 |
| | | MILDLY HYPOKINETIC | 2.5 TO 3.5 | 0 TO 90; 270 TO 360 |
| | | MODERATELY HYPOKINETIC | 1.5 TO 2.5 | 0 TO 90; 270 TO 360 |
| | | SEVERELY HYPOKINETIC | .5 TO 1.5 | 0 TO 90; 270 TO 360 |
| | | AKINETIC | 0 TO .5 | 0 TO 90; 270 TO 360 |
| | | DYSKINETIC | 1 TO 4 | 91 TO 269 |

FIG. 9

| SA CONFIGURATION | | | | |
|---|---|---|---|---|
| SEGMENT 1002 | DEFAULT SEGMENT NAME (CONFIGURABLE) 1004 | WALL MOTION SCORE (CONFIGURABLE) 1006 | DEFAULT AMPLITUDE M/S (CONFIGURABLE) 1008 | DEFAULT DIRECTION (DEGREES) (CONFIGURABLE) 1010 |
| 1 1012 | ANTERIOR | NORMAL 1014 | 3.5 TO 6.0 1026 | 180 TO 270 1038 |
| | | MILDLY HYPOKINETIC 1016 | 2.5 TO 3.5 1028 | 180 TO 270 1040 |
| | | MODERATELY HYPOKINETIC 1018 | 1.5 TO 2.5 1030 | 180 TO 270 1042 |
| | | SEVERELY HYPOKINETIC 1020 | .5 TO 1.5 1032 | 180 TO 270 1044 |
| | | AKINETIC 1022 | 0 TO .5 1034 | 180 TO 270 1046 |
| | | DYSKINETIC 1024 | 1 TO 4 1036 | 0 TO 179 1048 |
| 2 1050 | LATERAL | NORMAL | 3.5 TO 6.0 | 180 TO 360 |
| | | MILDLY HYPOKINETIC | 2.5 TO 3.5 | 180 TO 360 |
| | | MODERATELY HYPOKINETIC | 1.5 TO 2.5 | 180 TO 360 |
| | | SEVERELY HYPOKINETIC | .5 TO 1.5 | 180 TO 360 |
| | | AKINETIC | 0 TO .5 | 180 TO 360 |
| | | DYSKINETIC | 1 TO 4 | 0 TO 179 |
| 3 1052 | INFERO-LATERAL | NORMAL | 3.5 TO 6.0 | 90 TO 270 |
| | | MILDLY HYPOKINETIC | 2.5 TO 3.5 | 90 TO 270 |
| | | MODERATELY HYPOKINETIC | 1.5 TO 2.5 | 90 TO 270 |
| | | SEVERELY HYPOKINETIC | .5 TO 1.5 | 90 TO 270 |
| | | AKINETIC | 0 TO .5 | 90 TO 270 |
| | | DYSKINETIC | 1 TO 4 | 0 TO 89; 271 TO 360 |
| 4 1054 | INFERIOR | NORMAL | 3.5 TO 6.0 | 270 TO 360; 1 TO 180 |
| | | MILDLY HYPOKINETIC | 2.5 TO 3.5 | 270 TO 360; 1 TO 180 |
| | | MODERATELY HYPOKINETIC | 1.5 TO 2.5 | 270 TO 360; 1 TO 180 |
| | | SEVERELY HYPOKINETIC | .5 TO 1.5 | 270 TO 360; 1 TO 180 |
| | | AKINETIC | 0 TO .5 | 270 TO 360; 1 TO 180 |
| | | DYSKINETIC | 1 TO 4 | 181 TO 269 |
| 5 1056 | SEPTUM | NORMAL | 3.5 TO 6.0 | 0 TO 270 |
| | | MILDLY HYPOKINETIC | 2.5 TO 3.5 | 0 TO 270 |
| | | MODERATELY HYPOKINETIC | 1.5 TO 2.5 | 0 TO 270 |
| | | SEVERELY HYPOKINETIC | .5 TO 1.5 | 0 TO 270 |
| | | AKINETIC | 0 TO .5 | 0 TO 270 |
| | | DYSKINETIC | 1 TO 4 | 271 TO 360 |

FIG. 10

| 4 CH - 6 SEGMENT CONFIGURATION | | | | |
|---|---|---|---|---|
| SEGMENT | DEFAULT SEGMENT NAME (CONFIGURABLE) | WALL MOTION SCORE (CONFIGURABLE) | DEFAULT AMPLITUDE M/S (CONFIGURABLE) | DEFAULT DIRECTION (DEGREES) (CONFIGURABLE) |
| 1 | BASAL SEPTUM | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 191 TO 299 |
| 2 | MID SEPTUM | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 191 TO 299 |
| 3 | APICAL SEPTUM | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 91 TO 269 |
| 4 | BASAL LATERAL WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |
| 5 | MID LATERAL WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |
| 6 | APICAL LATERAL WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |

FIG. 11

| 2CH - 6 SEGMENT CONFIGURATION | | | | |
|---|---|---|---|---|
| SEGMENT | DEFAULT SEGMENT NAME (CONFIGURABLE) | WALL MOTION SCORE (CONFIGURABLE) | DEFAULT AMPLITUDE M/S (CONFIGURABLE) | DEFAULT DIRECTION (DEGREES) (CONFIGURABLE) |
| 1 | BASAL INFERIOR WALL | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 191 TO 299 |
| 2 | MID INFERIOR WALL | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 191 TO 299 |
| 3 | APICAL INFERIOR WALL | NORMAL | 3.5 TO 6.0 | 0 TO 190; 300 TO 360 |
| | | MILDLY HYPOKINETIC | 2.5 TO 3.5 | 0 TO 190; 300 TO 360 |
| | | MODERATELY HYPOKINETIC | 1.5 TO 2.5 | 0 TO 190; 300 TO 360 |
| | | SEVERELY HYPOKINETIC | .5 TO 1.5 | 0 TO 190; 300 TO 360 |
| | | AKINETIC | 0 TO .5 | 0 TO 190; 300 TO 360 |
| | | DYSKINETIC | 1 TO 4 | 91 TO 269 |
| 4 | BASAL ANTERIOR WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |
| 5 | MID ANTERIOR WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |
| 6 | APICAL ANTERIOR WALL | NORMAL | 3.5 TO 6.0 | 0 TO 30; 160 TO 360 |
| | | MILDLY HYPOKINETIC | 2.5 TO 3.5 | 0 TO 30; 160 TO 360 |
| | | MODERATELY HYPOKINETIC | 1.5 TO 2.5 | 0 TO 30; 160 TO 360 |
| | | SEVERELY HYPOKINETIC | .5 TO 1.5 | 0 TO 30; 160 TO 360 |
| | | AKINETIC | 0 TO .5 | 0 TO 30; 160 TO 360 |
| | | DYSKINETIC | 1 TO 4 | 31 TO 159 |

FIG. 12

ANATOMICAL FEATURE CONDITION ASSESSMENT SYSTEM USING TISSUE DISPLACEMENT CHARACTERISTICS

This is a non-provisional application of provisional application Ser. No. 60/746,664 by M. P. Esham et al. filed May 8, 2006.

FIELD OF THE INVENTION

The present invention relates to anatomical feature condition assessment systems, and in particular to heart wall movement assessment systems.

BACKGROUND OF THE INVENTION

Currently, assessments of anatomical features, and in particular the motion of the walls of the left ventricle of human hearts may be performed by the subjective valuation by humans of the motion of individual wall segments. That is, an ultrasound or echocardiogram video of a moving left ventricle may be recorded for later analysis and/or observed in real time. A clinician observes the video, divides the observed wall of the ventricle into segments, and evaluates the motion of each segment to produce a wall motion score. Because different clinicians may segment the wall of the left ventricle differently, and score the movement of the segments differently, there is a difficulty in accurately reproducing assessment scores by different people based on the same data.

Systems have been developed which assist clinicians in scoring wall movement. Such systems process the ultrasound video to identify portions of the video corresponding to a desired wall and then evaluate the motion of the identified wall. This may require human interaction, or may be done automatically. Some such systems automatically segment the wall and color code the wall segment according to the instantaneous motion of the segment. Other such systems calculate motion vectors, identifying motion velocity and direction, for respective points on the identified wall. A motion display is overlaid atop the ultrasound video display. The display includes a set of lines respectively corresponding to points on the identified wall. The length of the lines indicate the speed and the angle of the lines indicate the direction of the motion of the corresponding point. Such systems aid a clinician in producing a wall motion score, but subjective evaluation is still required.

Further systems have been developed to automatically generate a wall motion score. Such systems estimate the motion of segments of a left ventricle wall by comparing a maximum and a minimum displacement of the segment wall. A score for each segment is then calculated. However, the accuracy of calculating wall motion by displacement is less than that of calculating wall motion based on the motion velocity and direction of wall segments.

The inventors have advantageously recognized it is desirable to remove the subjective element in generating a wall motion score while maximizing the accuracy of such an assessment. This will result in more uniformity and reproducibility in wall motion scores and will increase the value of a series of such scores across a plurality of patients or over time relating to a single patient.

BRIEF SUMMARY OF THE INVENTION

In accordance with principles of the present invention, an anatomical feature condition assessment system includes an acquisition processor for acquiring data representing the velocity and direction measurements of individual segments of an anatomical feature of a patient. A repository contains mapping data associating averaged velocity and direction measurements within a predetermined particular segment of the anatomical feature with a set of values. A data processor averages the acquired velocity and direction measurements within the predetermined particular segment of the anatomical feature and uses the mapping data to identify a set of values associated with the averaged acquired velocity and direction measurements. The data processor uses the identified set of values to derive an assessment of the condition of the anatomical feature of the patient.

BRIEF DESCRIPTION OF THE DRAWING

In the drawing:

FIG. 8, FIG. 9, FIG. 10, FIG. 11 and FIG. 12 illustrate tables of information which are stored in a repository in FIG. 1 and used during the operation of the system of FIG. 1 according to the present invention.

DETAILED DESCRIPTION OF THE INVENTION

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprises any combination of, hardware, firmware, and/or software.

An executable application, as used herein, comprises code or machine readable instructions for conditioning the processor to implement predetermined functions, such as those of an operating system, an anatomical feature condition assessment system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

Velocity vector imaging (VVI), as used herein, comprises apparatus and methods for measuring the velocity and direction of movement of a location on an anatomical feature, and in particular on the wall of a muscle, e.g. a heart muscle. This data is typically used to overlay a video of a view of the human heart beating with indicators representing the velocity, i.e. the velocity and direction, of points on a wall of the heart.

Figure 1:
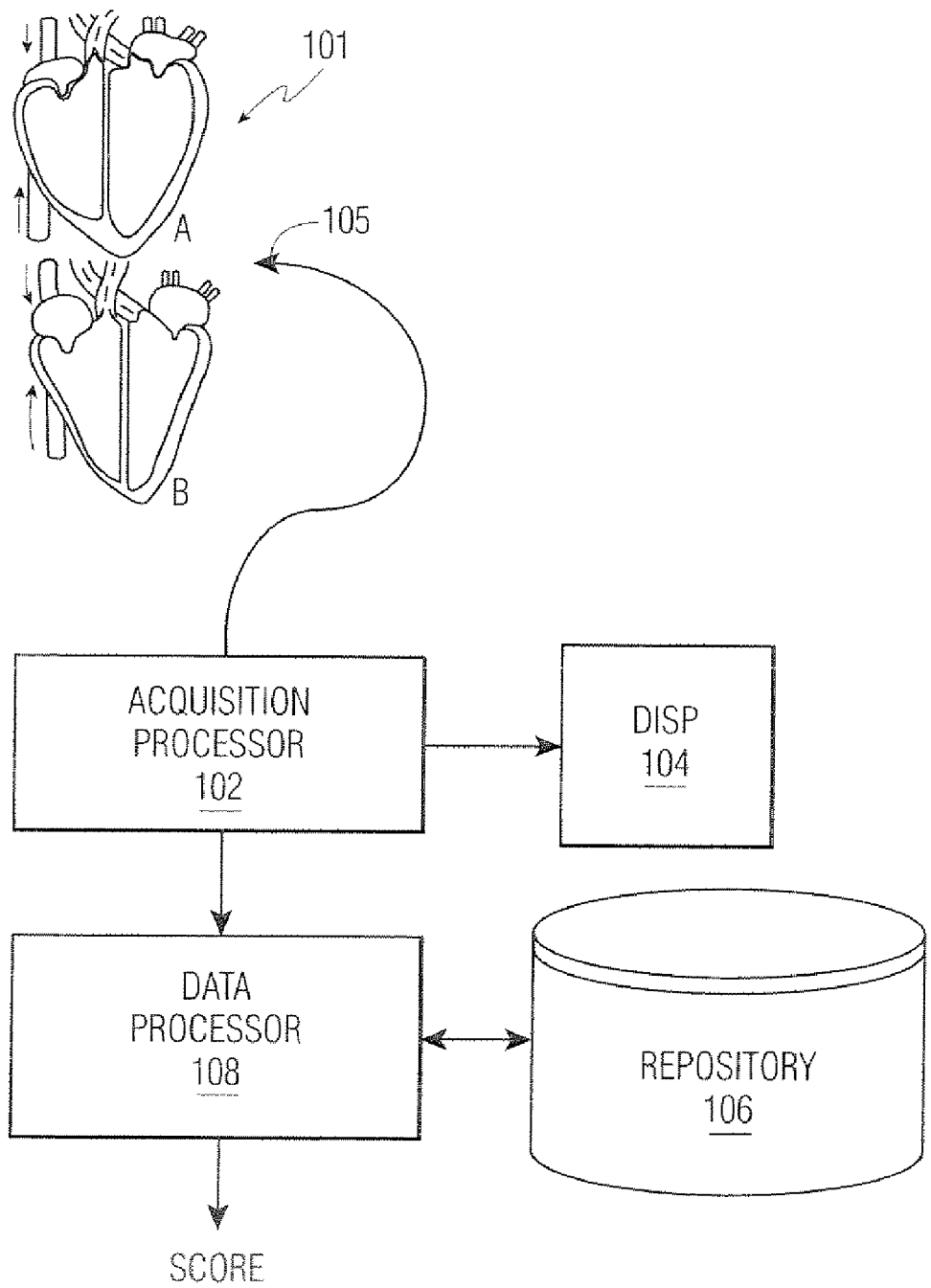
FIG. 1 is a block diagram of a system for anatomical feature condition assessment according to the present invention.

FIG. 1 is a block diagram of a system for anatomical feature condition assessment according to the present invention. In FIG. 1, a measurement probe 105 is used to collect data representing an anatomical feature 101 of a patient. The measurement probe 105 is coupled to an input terminal of an acquisition processor 102. A first output terminal of the acquisition processor 102 is coupled to a display device 104. A second output terminal of the acquisition processor 102 is coupled to an input terminal of a data processor 108. A repository 106 is bidirectionally coupled to a corresponding terminal of the data processor 108. An output terminal of the data processor 108 produces a score representing the assessment of the condition of the anatomical feature of the patient. The output terminal is coupled to a utilization means (not shown) for displaying, printing, saving or otherwise utilizing the score.

In general, the acquisition processor 102 acquires data representing velocity and direction measurements of individual segments of an anatomical feature of a patient. The data processor 108 averages the acquired velocity and direction measurements within the predetermined particular segment of the anatomical feature. The repository 106 contains mapping data associating averaged velocity and direction measurements within a predetermined particular segment of the anatomical feature with a set of values. More specifically, the repository contains mapping data associating ranges of averaged velocity and direction measurements within a predetermined particular segment of the anatomical feature with respective ones of a set of values. The data processor 108 uses the mapping data to identify a set of values associated with the averaged acquired velocity and direction measurements, and uses the identified set of values to derive an assessment of the condition of the anatomical feature of the patient.

In the illustrated embodiment, the anatomical feature being assessed is a wall in a human heart, and in particular, the motion of the left ventricle of a human heart 101. The assessment derived by the data processor 108 is a wall motion scoring value. The motion scoring value is derived completely in the data processor 108 and is derived independently of human observation. In the illustrated embodiment the identified set of values comprises: (a) normal; (b) mildly hypokinetic; (c) moderately hypokinetic; (d) severely hypokinetic; (e) akinetic; and (f) dyskinetic.

In FIG. 1, the acquisition processor 102 may be an ultrasound or echocardiogram or other similar device capable of generating data representing a moving image of the left ventricle of the human heart 101. The ultrasound or echocardiogram device 102 displays time-sequential images, forming a video image, of the human heart 101 on the display device 104. The acquisition processor 102 includes the function of detecting in the video image an outline of a portion of the human heart, e.g. the wall of the left ventricle; generating data representing velocity and direction measurements of individual locations on the detected outline; and displaying the outline and the velocity and direction measurement data in the video image on the display device 104

Figure 2:
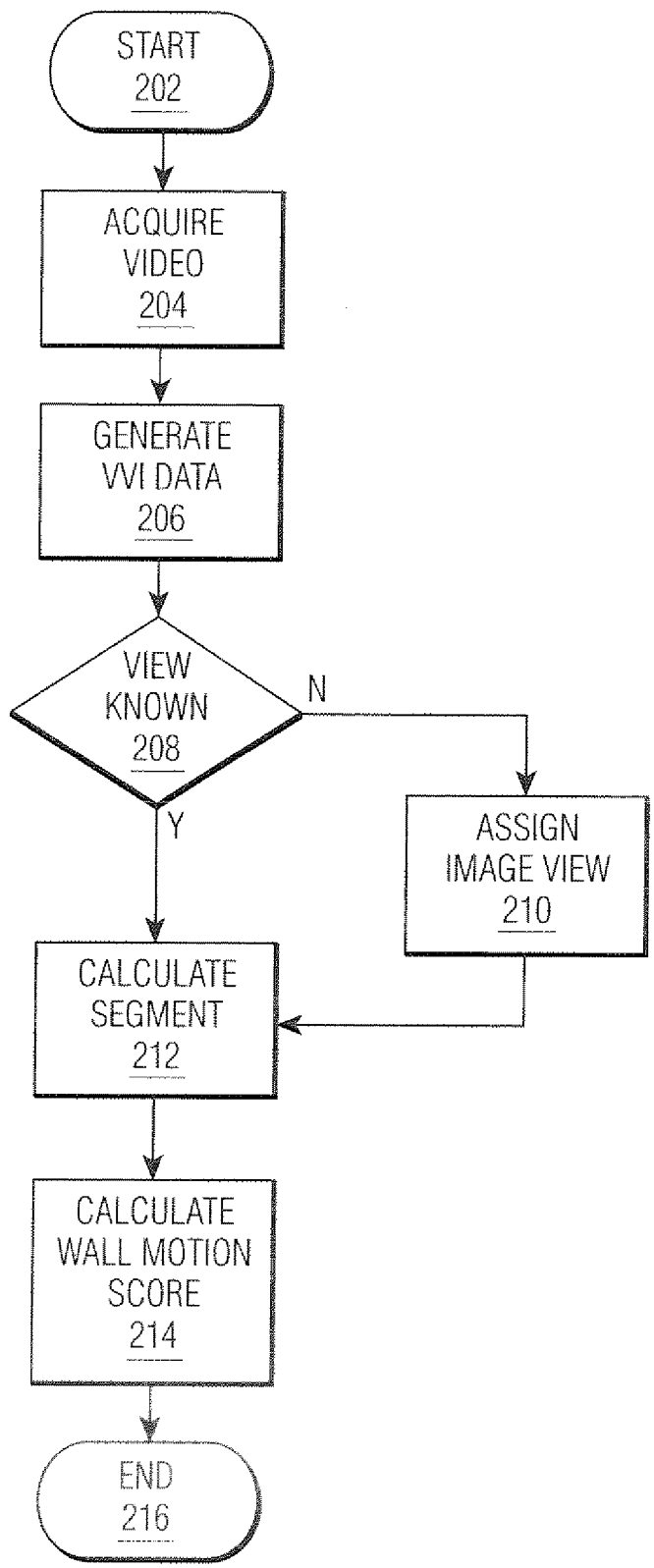
FIG. 2 is a flowchart illustrating the operation of the system of FIG. 1 according to the present invention.

FIG. 2 is a flowchart useful in understanding details in the operation of the system illustrated in FIG. 1. Referring concurrently to FIG. 1 and FIG. 2, the system starts at block 202. In block 204, the acquisition processor 102 acquires data representing a video of a section of a human heart 101. In block 206, velocity vector imaging (VVI) data is derived. The VVI data represents speed and direction (i.e. the velocity vector) at a plurality of points on an anatomical feature in a patient.

Figure 3A:
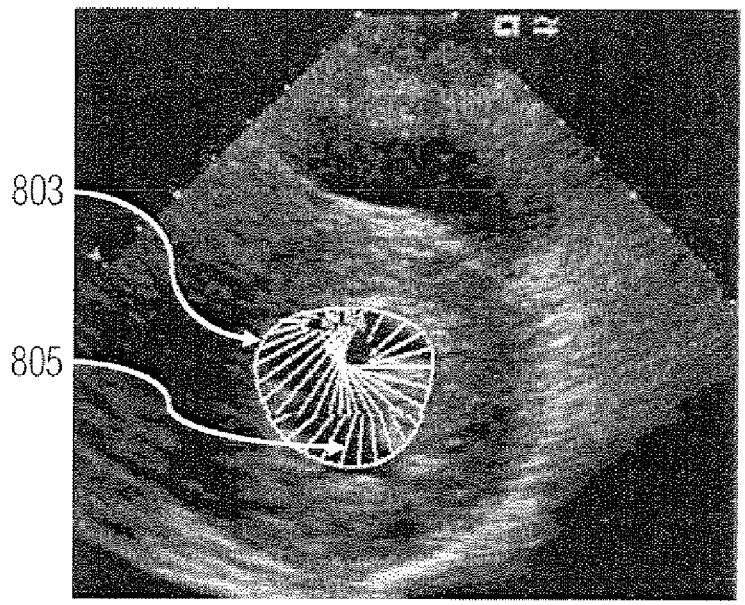
FIG. 3a and FIG. 3b show respective ultrasound images of a view of a left ventricle of a human heart with velocity vector imaging overlaid on it, as may be displayed by the system of FIG. 1 according to the present invention.
Figure 3B:
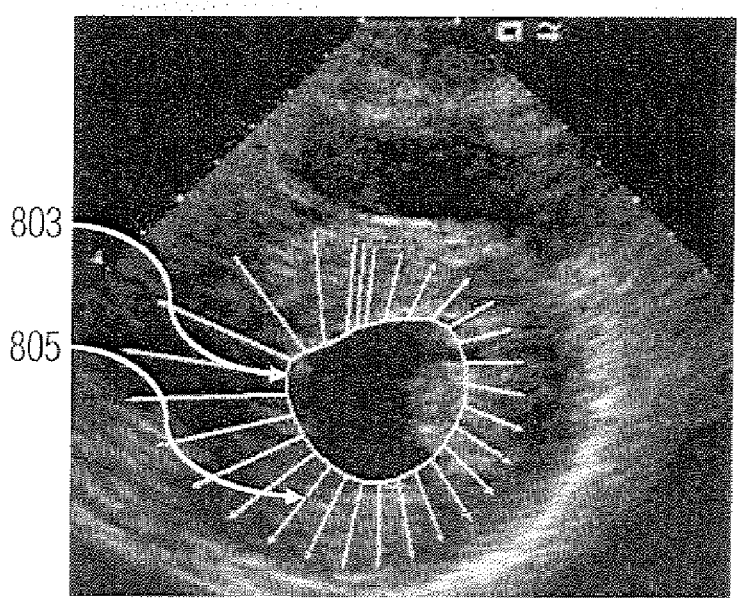

FIG. 3 shows two ultrasound images extracted from a video of the motion of the left ventricle of a human heart. More specifically, FIG. 3 shows images of a parasternal short axis view of a left ventricle of a human heart. VVI data has been overlaid atop the ultrasound images. In FIG. 3, a peripheral line 803 is overlaid on the portion of the image representing the periphery of the left ventricle wall. Straight lines, e.g. 805, have a first end anchored along the peripheral line 803. The lines, e.g. 805, have an angle and length. The angle of the lines, e.g. 805, indicates the instantaneous direction of motion of the location of the peripheral line 803 to which that line is anchored. The length of the lines, e.g. 805, indicates the velocity of motion of the location of the peripheral line 803 to which that line is anchored. FIG. 3a shows a time during the contraction of the left ventricle, indicated by the direction of motion of the peripheral line 803 being inward, and FIG. 3b shows a time during the expansion of the left ventricle, indicated by the motion of the peripheral line 803 being outward.

The acquired VVI data, represents the velocity and direction measurements at a plurality of locations within individual segments of the anatomical feature of the patient, i.e. within segments of a left ventricle wall. The assessment system (FIG. 1) can automatically derive an assessment of the anatomical feature based on a recognized view of the anatomical feature. Referring to the wall motion score for the left ventricle, there are several views of the left ventricle which are typically observed.

Figure 4:
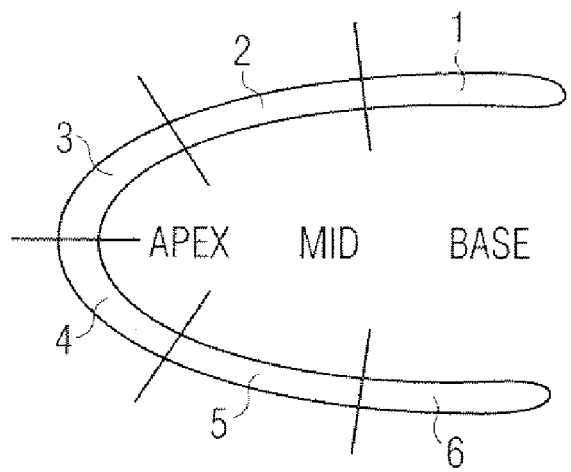
FIG. 4, FIG. 5, FIG. 6 and FIG. 7 are schematic diagrams illustrating respective views of the left ventricle of a human heart partitioned into segments, as may be seen on the display device of an acquisition processor in a system of FIG. 1 according to the present invention.
Figure 5:
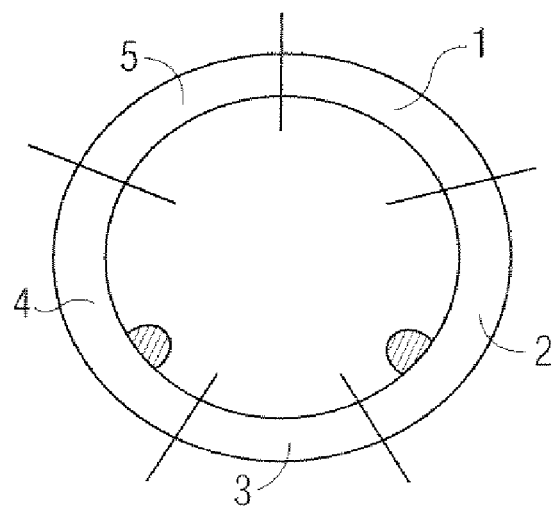
Figure 6:
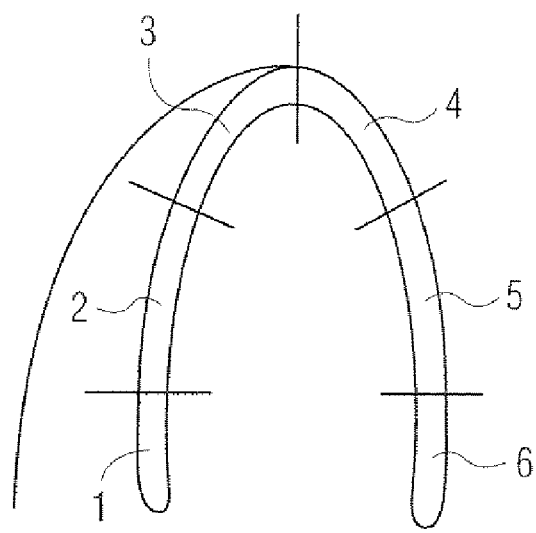
Figure 7:
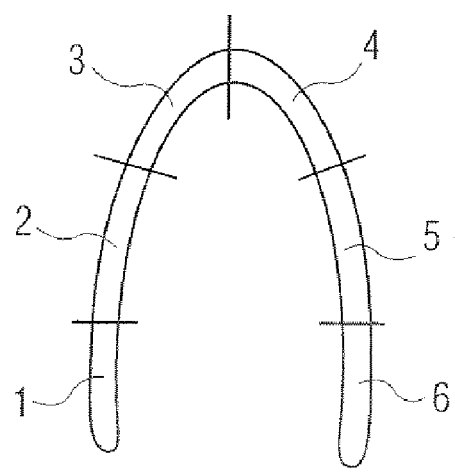

A first view is a parasternal long axis view (PLAX). Such a view is schematically illustrated in FIG. 4. Depending on the slice of the left ventricle being observed, the left ventricle wall in the PLAX view may be divided into 4 or 6 segments. The table in FIG. 4 shows data used to illustrate how the observed left ventricle wall in the PLAX view is divided into segments. The left ventricle illustrated in FIG. 4 is divided into 6 segments numbered 1 to 6 in order from upper right to lower right. A second view is a parasternal short axis view (SA). Such a view is schematically illustrated in FIG. 5. The left ventricle illustrated in FIG. 5 is divided into 5 segments numbered 1 to 5 starting at the top in clockwise order. Another view is a 4 chamber (4ch) view. Such a view is schematically illustrated in FIG. 6. The left ventricle illustrated in FIG. 6 is divided into 6 segments numbered 1 to 6 in order from the lower left to the lower right. Another view is a 2 chamber (2ch) view. Such a view is schematically illustrated in FIG. 7. The left ventricle illustrated in FIG. 7 is divided into 6 segments numbered 1 to 6 in order from lower left to lower right. Ultrasonic data representing a video of a left ventricle in one of the above typical views may be automatically divided into segments. Automatic dividing of an image of the left ventricle wall may also be performed in other views.

As illustrated in FIG. 3, VVI data is generated for a plurality of points on the wall of the left ventricle. In order to properly divide the observed portion of the left ventricle into segments, the view represented by the acquired data needs to be one that is recognizable by the system (FIG. 1). In block 208 (FIG. 2), the observed view is checked to verify that it is a view recognizable to the system. If not, then in block 210 the probe 105 is moved until a recognizable view is obtained. In block 212, the velocity and direction measurements are acquired for respective locations within the respective individual segments of the anatomical feature, e.g. left ventricle wall. The acquired velocity and direction measurements within a predetermined particular segment of the anatomical feature, e.g. left ventricle wall, are averaged to produce averaged acquired velocity and direction measurement for the segment. This is repeated for the respective segments.

In block 214 (FIG. 2), the left ventricle wall motion score is calculated. As described above, the repository 106 (FIG. 1) maintains mapping data associating averaged velocity and direction measurements within a predetermined particular segment of the anatomical feature, e.g. left ventricle wall, with a set of values. Such mapping data is illustrated in FIG. 8, FIG. 9, FIG. 10, FIG. 11 and FIG. 12. The data processor 108 uses the mapping data to identify a set of values associated with the averaged acquired velocity and direction measurements. From these identified sets of values, an assessment, e.g. a score value, of the condition of the anatomical feature of the patient is derived. The score value is provided at the output terminal of the system, and may be evaluated by a clinician.

For example, the VVI data illustrated in FIG. 3 is supplied to the data processor 108 (FIG. 1). The data processor 108 determines in block 208 (FIG. 2) that the observed view of the left ventricle is the parasternal short axis view (SA). Because this is a known, typical, view, the observed wall may be divided automatically into segments as illustrated in FIG. 5. The VVI data illustrated in FIG. 3 within the respective segments is averaged to derive an average velocity and direction measurement associated with that segment. The SA configuration table (FIG. 10) includes information for the respective segments relating the average velocity and direction acquired for that section to a motion score value for that section.

More specifically in the SA configuration table (FIG. 10) respective rows represent a score value for a corresponding segment. In FIG. 10, the first column 1002 lists the segment number, corresponding to the segments illustrated in FIG. 5. The second column 1004 contains a name for the corresponding segment. These may be changed by a user. The third column contains motion scores for the corresponding segment. These identified sets of values, e.g. motion scores, are: (a) normal 1014, meaning the wall thickens normally; (b) mildly hypokinetic 1016 meaning the wall thickens subtly less than normal; (c) moderately hypokinetic 1018 meaning there is a noticeable lack of thickening of the wall segment; (d) severely hypokinetic 1020 meaning there is almost no thickening of the wall segment; (e) akinetic 1022 meaning the wall does not move, there is no thickening of the wall segment; and (f) dyskinetic 1024 meaning the wall segment moves away from the left ventricular cavity during systole, i.e. in the opposite direction it should be moving. These scores may also be changed by a user.

The fourth column 1008 contains a set of values representing ranges of the average acquired velocity for segment 1 respectively corresponding to wall motion score values in the third column 1006. Similarly, the fifth column 1010 contains a set of values representing ranges of the average acquired direction for segment 1 respectively corresponding to the wall motion score values in the third column 1006. For example, a range 1026 of 3.5-6.0 meters per second (m/s) and a range 1038 of direction from 180-270 degrees corresponds to a 'normal' wall motion score 1014; a range 1028 of 2.5-3.5 m/s and a range 1040 of 180-270 degrees corresponds to a 'mildly hypokinetic' wall motion score 1016, and so forth. These ranges may be changed by a user.

The first row 1012 of the SA configuration table (FIG. 10) is associated with segment 1 of the left ventricle wall, e.g. the upper left segment as illustrated in FIG. 5; the second row 1050 is associated with segment 2; the third row 1052 is associated with segment 3, and so forth.

In block 214 (FIG. 2) the data processor 108 (FIG. 1) compares the average velocity and direction calculated, as described above, for segment 1 to the values in the fourth and fifth columns, 1008 and 1010 respectively. For example, if the average acquired velocity derived for segment 1 is 5.2 m/s, and the direction is 210 degrees, this falls into the ranges 1026 and 1038 respectively and are associated with a 'normal' wall motion score 1014 for the 'anterior' segment, e.g. segment 1. If the average acquired velocity is 3.5 m/s and the direction is 120 degrees, this falls into the ranges 1036 and 1048 respectively, and are associated with the 'dyskinetic' wall motion score 1024 for the 'anterior' segment, e.g. segment 1.

Average acquired velocity and direction measurements for the remaining segments, i.e. segments 2-5, are compared to the ranges listed in the fourth and fifth columns, 1008 and 1010, in a similar manner. That is, the calculated average acquired velocity and direction measurements for a segment are compared to the amplitude and direction ranges (1008 and 1010), in the row corresponding to that segment. The result of the comparison determines which wall motion score (1006) is associated with that segment. For segment 2, the data in columns 1008 and 1010 of row 1050 is used; for segment 3, the data in columns 1008 and 1010 of row 1052 is used, and so forth. For example, if the average acquired velocity derived for segment 3 (row 1052) is 5.2 m/s and the direction is 210 degrees, this falls into the range associated with a 'normal' wall motion score for the 'lateral' segment; while if the average acquired velocity derived for segment 4 (row 1054) is 3.2 m/s and the direction is 120 degrees, this falls into the range associated with a 'dyskinetic' wall motion score for the 'inferior' segment.

The data processor 108 (FIG. 1) performs step 214 (FIG. 2) for the respective segments in the assigned image view (block 210) to derive an assessment for the anatomical feature, e.g. left ventricle wall motion. This assessment consists of a wall motions score (i.e. normal, mildly hypokinetic, moderately hypokinetic, severely hypokinetic, akinetic, dyskinetic) for the respective segments (i.e. anterior, lateral, infero-lateral, inferior, septum) in the view. This data may be communicated and/or stored in any format. It may be displayed in table format or any other similar format useful in evaluating such data. For example, Table 1 (below) illustrates an example of a report of an assessment of a left ventricle wall motion for a patient in table format. One skilled in the art will understand how to store and communicate such data, and how to format a display of such information in a manner to best enable a clinician to understand and use the assessment.

TABLE 1

Left Ventricle Wall Motion Score
SA Configuration

| Anterior | Mildly hypokinetic |
|---|---|
| Lateral | Mildly hypokinetic |
| Infero-lateral | Moderately hypokinetic |
| Inferior | Severely hypokinetic |
| Septum | Moderately hypokinetic |

Similarly, the data processor 108 (FIG. 1) performs the same processing for VVI data derived from the other typical views: i.e. for a PLAX-4 segment view using the data in table in FIG. 8; PLAX-6 segment view using the data in table in FIG. 9; 4-ch 6 segment view using the data in table in FIG. 11; and 2-ch 6 segment view using the data in table FIG. 12.

The wall motion score may be sent back to the acquisition processor 102 which, in turn displays the score on the display device 104. Alternatively, the score may be displayed on a different display device, and/or communicated to a central station (not shown) having a storage device for accumulating and storing medical data about the patient.

Although described in terms of using ultrasound to derive data representing the motion of the left ventricle of a human heart, one skilled in the art understands that any similar patient monitoring/evaluation system capable of generating data representing the motion of predetermined particular segments of a left ventricle may be used.

Further, although the written description above is directed to the assessment of the wall motion of the left ventricle of a human heart, one skilled in the art understands that this system is applicable to the assessment of any similar anatomical feature.

What is claimed is:

1. An anatomical feature condition assessment system, comprising:
   an acquisition processor configured for acquiring data representing velocity and direction measurements of individual segments of an anatomical feature of a patient;
   a repository of mapping data associating a predetermined reference range of averaged velocity measurements and a predetermined reference range of angular direction measurements within a predetermined particular segment of said anatomical feature with a set of values indicative of medical conditions; and
   a data processor configured for averaging the acquired velocity and direction measurements within said predetermined particular segment of said anatomical feature and using said predetermined reference range of averaged velocity measurements and said predetermined reference range of angular direction measurements to identify a set of values associated with the averaged acquired velocity and direction measurements of the predetermined particular segment and using the identified set of values to determine a medical condition of the anatomical feature of the patient.

2. A system according to claim 1, wherein the data processor further divides said averaged acquired velocity and the averaged direction measurements into segments corresponding to said individual segments of said anatomical feature and averages said acquired velocity and direction measurements within said individual segments of said anatomical feature.

3. A system according to claim 1, wherein said identified set of values comprises (a) normal (b) mildly hypokinetic; (c) moderately hypokinetic; (d) severely hypokinetic; (e) akinetic; and (f) dyskinetic.

4. A system according to claim 3, wherein said repository contains mapping data associating a plurality of predetermined reference ranges of averaged velocity and direction measurements within said predetermined particular segment of said anatomical feature with respective ones of said set of values.

5. A system according to claim 1, wherein said anatomical feature is a wall in a human heart.

6. A system according to claim 1, wherein said anatomical feature is a wall in a human heart, and said assessment is a wall motion scoring value.

7. A system according to claim 6, wherein said motion scoring value is derived independently of human observation.

8. A system according to claim 7, wherein said anatomical feature is a wall in a human heart and said motion scoring value is derived independently of human observation.

9. A method for assessing the condition of an anatomical feature, comprising:
   using at least one processor device for,
      acquiring data representing velocity and direction measurements within individual segments of an anatomical feature of a patient;
      averaging acquired velocity and direction measurements within a predetermined particular segment of said anatomical feature;
      storing mapping data associating a predetermined reference range of averaged velocity measurements and a predetermined reference range of angular direction measurements within a predetermined particular segment of the anatomical feature with a set of values indicative of medical conditions;
      using said predetermined reference of averaged velocity measurements and said predetermined reference range of angular direction measurements of the predetermined particular segment to identify a set of values associated with the averaged acquired velocity and direction measurements;
      using said identified set of values to determine a medical condition of the anatomical feature of the patient.

10. An anatomical feature condition assessment system, comprising:
   a means for acquiring data representing velocity and direction measurements of individual segments of an anatomical feature of a patient;
   a repository of mapping data associating a predetermined reference range of averaged velocity measurements and a predetermined reference range of angular direction measurements within a predetermined particular segment of said anatomical feature with a set of values indicative of medical conditions; and
   a means for averaging the acquired velocity and direction measurements within said predetermined particular segment of said anatomical feature and using said predetermined reference range of averaged velocity measurements and said predetermined reference range of angular direction measurements to identify a set of values associated with the averaged acquired velocity and direction measurements of the predetermined particular segment and using the identified set of values to derive an assessment of the condition of the anatomical feature of the patient.

* * * * *